(12) United States Patent
Keller et al.

(10) Patent No.: US 6,461,591 B1
(45) Date of Patent: Oct. 8, 2002

(54) MEDICAL AEROSOL FORMULATIONS

(75) Inventors: Manfred Keller, Bad Krozingen (DE); Kurt Herzog, Basel (CH)

(73) Assignee: Jago Research AG, Muttenz (CH)

( * ) Notice: Subject to any disclaimer, the term of this patent is extended or adjusted under 35 U.S.C. 154(b) by 0 days.

(21) Appl. No.: 09/355,883

(22) PCT Filed: Feb. 2, 1998

(86) PCT No.: PCT/CH98/00037

§ 371 (c)(1), (2), (4) Date: Aug. 4, 1999

(87) PCT Pub. No.: WO98/34595

PCT Pub. Date: Aug. 13, 1998

(30) Foreign Application Priority Data

Feb. 5, 1997 (CH) .............................................. 0248/97

(51) Int. Cl.$^7$ ........................... A61K 9/12; A61K 31/00; A61K 47/00

(52) U.S. Cl. ..................... 424/45; 514/177; 514/263.34; 514/374; 514/471; 514/490; 514/506; 514/646; 514/693; 514/699; 514/721; 514/728; 514/730; 514/731; 514/736; 514/738; 514/772; 514/957; 514/958

(58) Field of Search ............................ 424/45; 514/957, 514/958, 975, 177, 263.34, 374, 471, 490, 506, 646, 643, 699, 721, 728, 730, 731, 736, 738, 772

(56) References Cited

U.S. PATENT DOCUMENTS

| | | | |
|---|---|---|---|
| 2,868,691 A | 1/1959 | Porush et al. ................ 222/192 |
| 3,014,844 A | 12/1961 | Thiel et al. ..................... 424/46 |
| 4,139,617 A | 2/1979 | Simons et al. ................. 424/45 |
| 4,174,295 A | 11/1979 | Bargigia et al. ................ 516/8 |
| 5,225,183 A | * 7/1993 | Purewal et al. ................ 424/45 |
| 5,698,630 A | * 12/1997 | Andersson ..................... 252/8 |

FOREIGN PATENT DOCUMENTS

| | | | |
|---|---|---|---|
| CA | 2075058 | | 1/1991 |
| CA | 2062854 | | 3/1992 |
| CA | 2068492 | | 12/1992 |
| DE | 2736500 | | 2/1978 |
| EP | 0372777 | | 6/1990 |
| EP | 0504112 | | 3/1992 |
| EP | 0550031 | | 12/1992 |
| JP | 61158919 | | 7/1986 |
| WO | 9104011 | | 4/1991 |
| WO | 9111495 | | 8/1991 |
| WO | 9200061 | | 1/1992 |
| WO | 9317335 | | 9/1993 |
| WO | 94/01511 | * | 1/1994 |
| WO | 94/03056 | * | 2/1994 |
| WO | 96/19198 | * | 6/1996 |

OTHER PUBLICATIONS

RD–17066, Aerosol propellants comprising N2O and/or CO2 (Jun. 1978), Research Disclosure (170), p. 58.*
XP 002039615, Aerosol pressure packs for administration of medicaments (1989), WPI/DERWENT, Abstract.*
Derwent Publication No. AN–89–184245, Aerosol Pressure Packs for Administration of Medicaments—Contain Propellants Such as Hydrocarbons(s), Carbond Dioxide, Nitrogen etc. and/or Fluoro:Hydrocarbons(s) (1989).

* cited by examiner

*Primary Examiner*—Jose' G. Dees
*Assistant Examiner*—Frank Choi
(74) *Attorney, Agent, or Firm*—Selitto, Behr & Kim

(57) ABSTRACT

A pressure-liquefied propellant mixture for aerosols, comprising a fluorinated alkane, in particular 1,1,1,2-tetrafluoroethane and/or 1,1,1,2,3,3,3-heptafluoropropane, and carbon dioxide, makes possible an improvement of the wetting properties of pharmaceutically active compounds, with which the formulation problems existing with hydrofluoroalkanes in relation to suspension as well as solution aerosols can be overcome and thus improved medicinal aerosol formulations can be obtained. With the aid of carbon dioxide, it is also possible to specifically influence the pressure and thus the particle size distribution and also by displacement of oxygen from the hydrofluoroalkanes to improve the storage stability of oxidation-sensitive active compounds.

18 Claims, 6 Drawing Sheets

MEDICAL AEROSOL FORMULATIONS

Figure 1A:
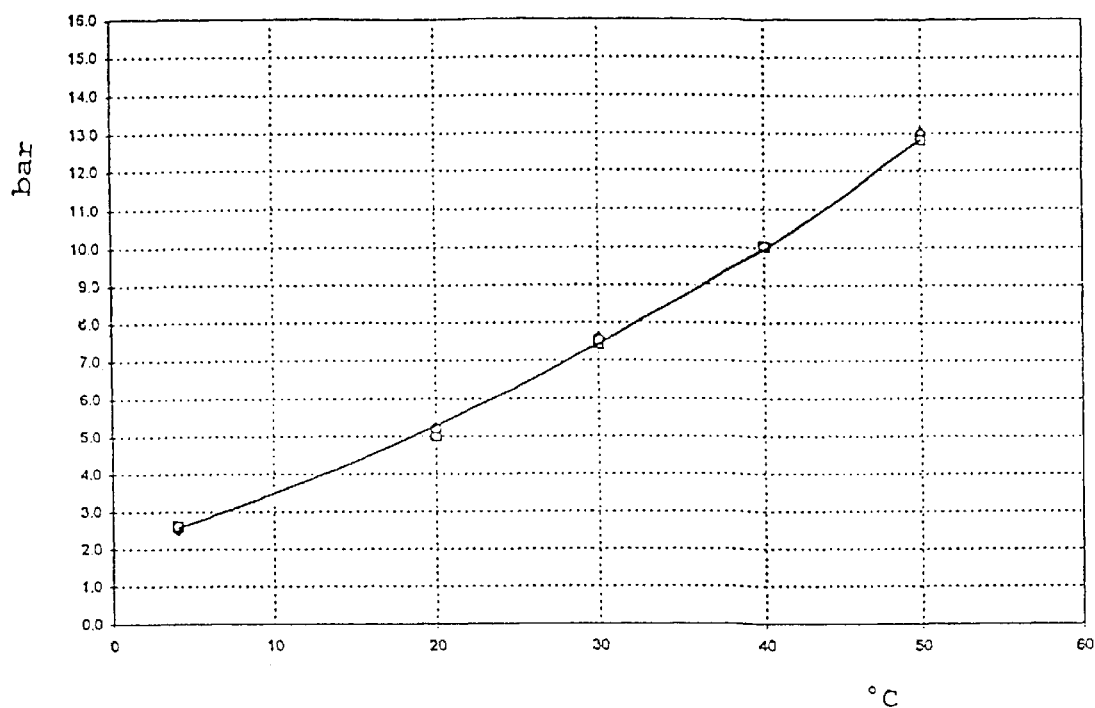
Figure 1B:
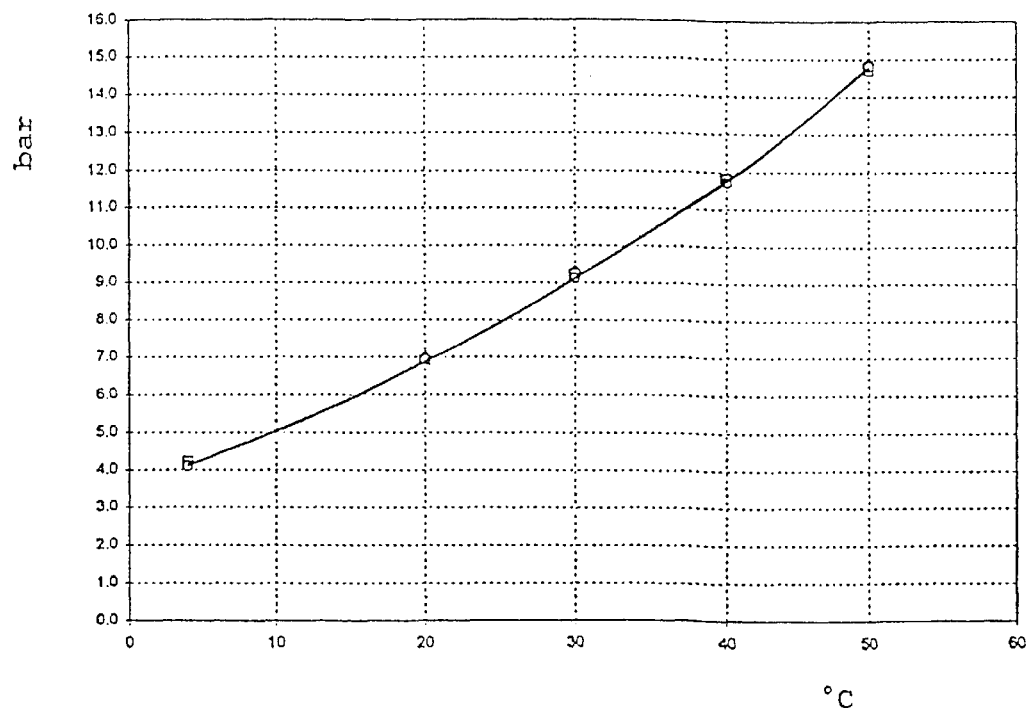
Figure 2A:
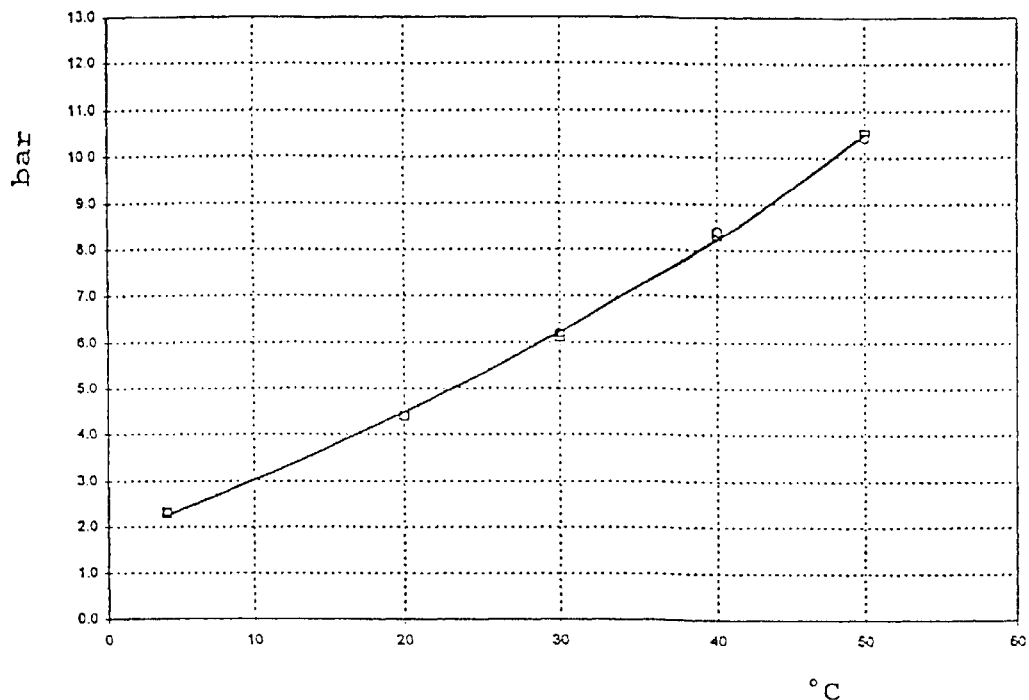
Figure 2B:
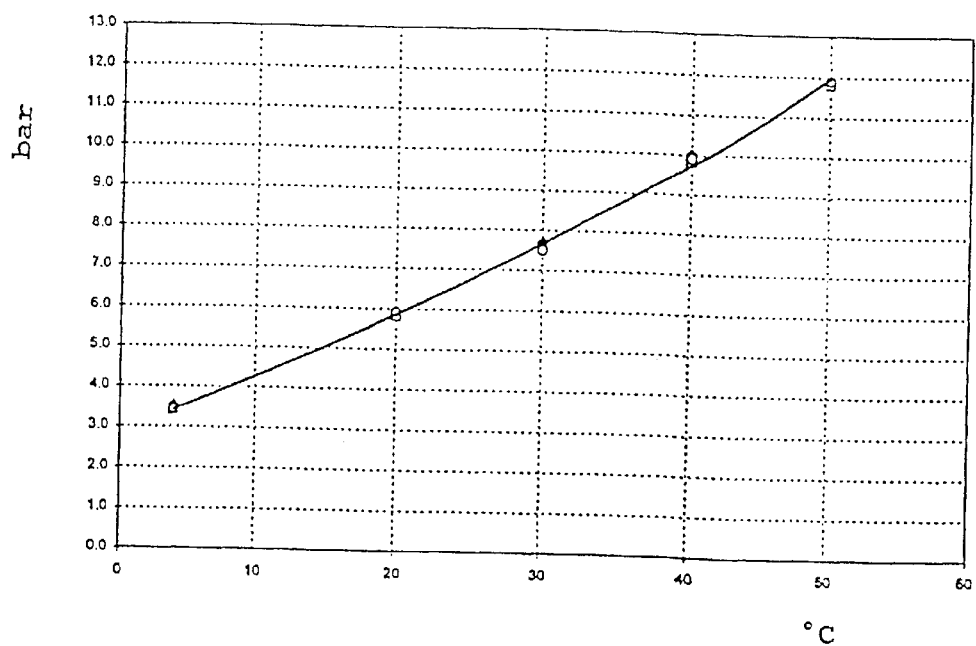
Figure 3A:
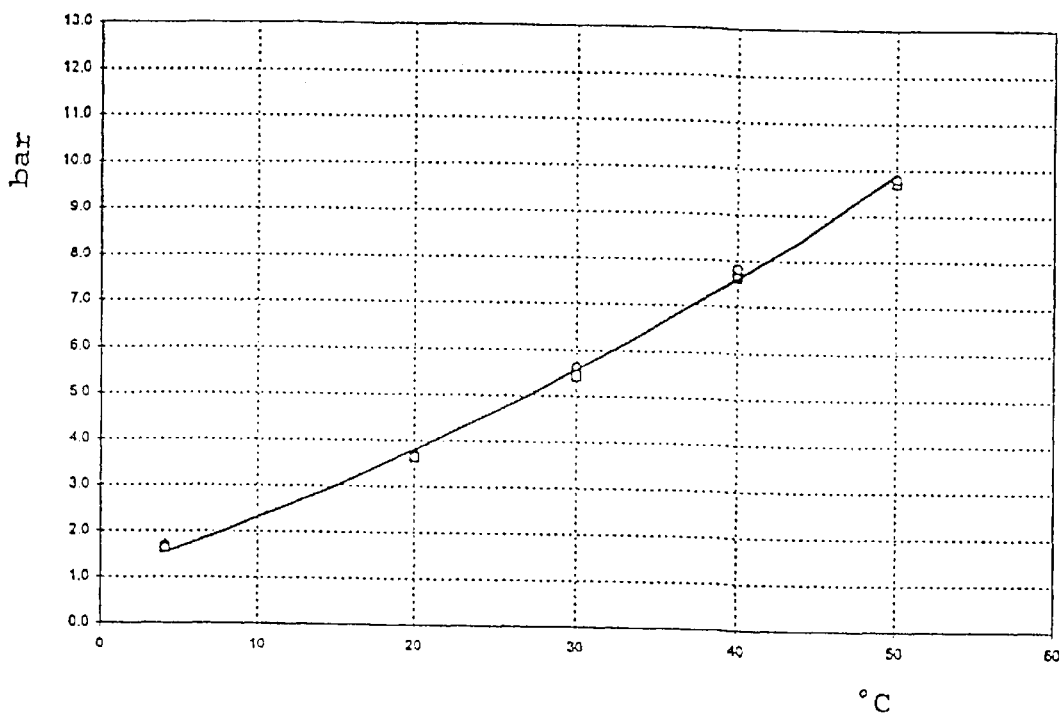
Figure 3B:
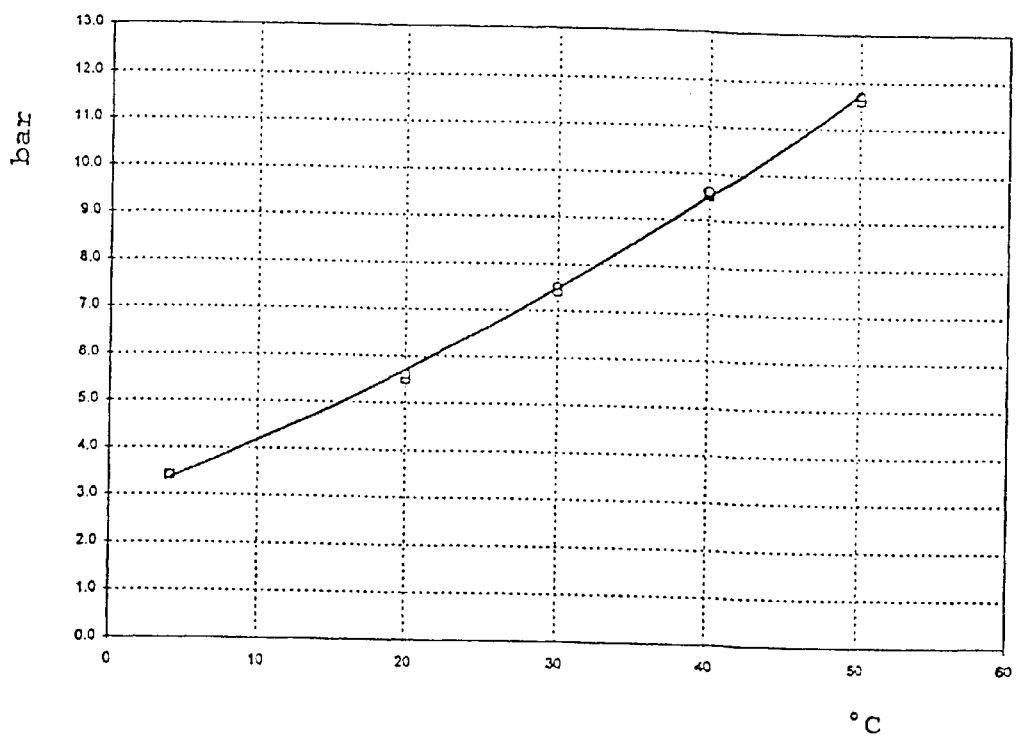
Figure 4A:
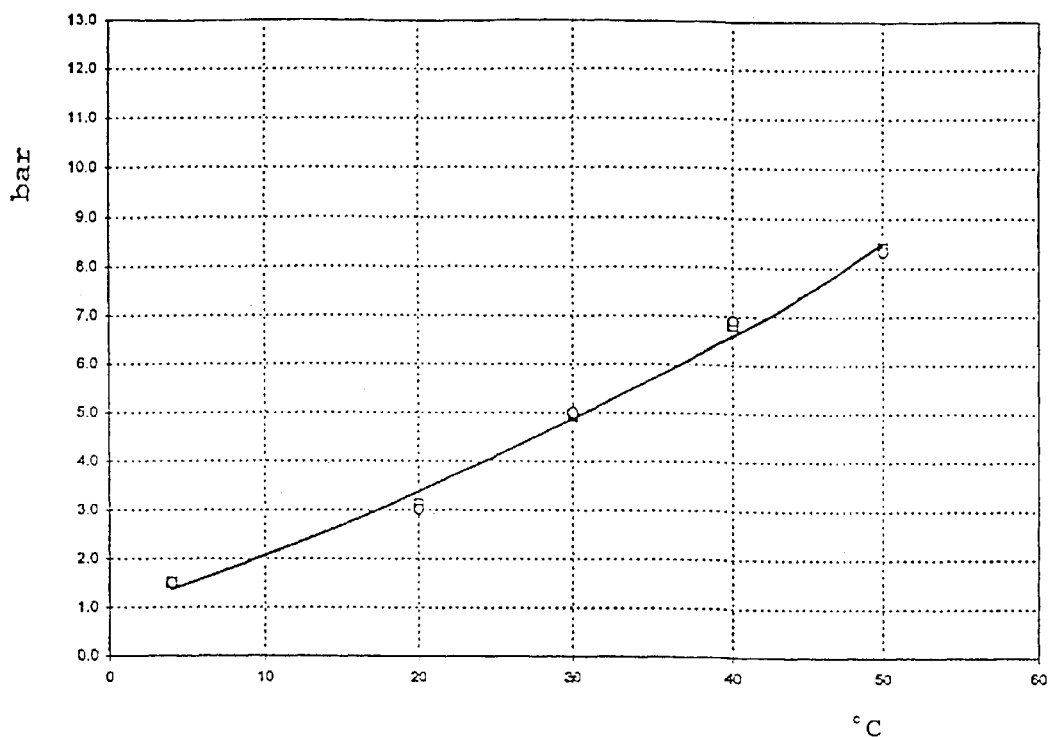
Figure 4B:
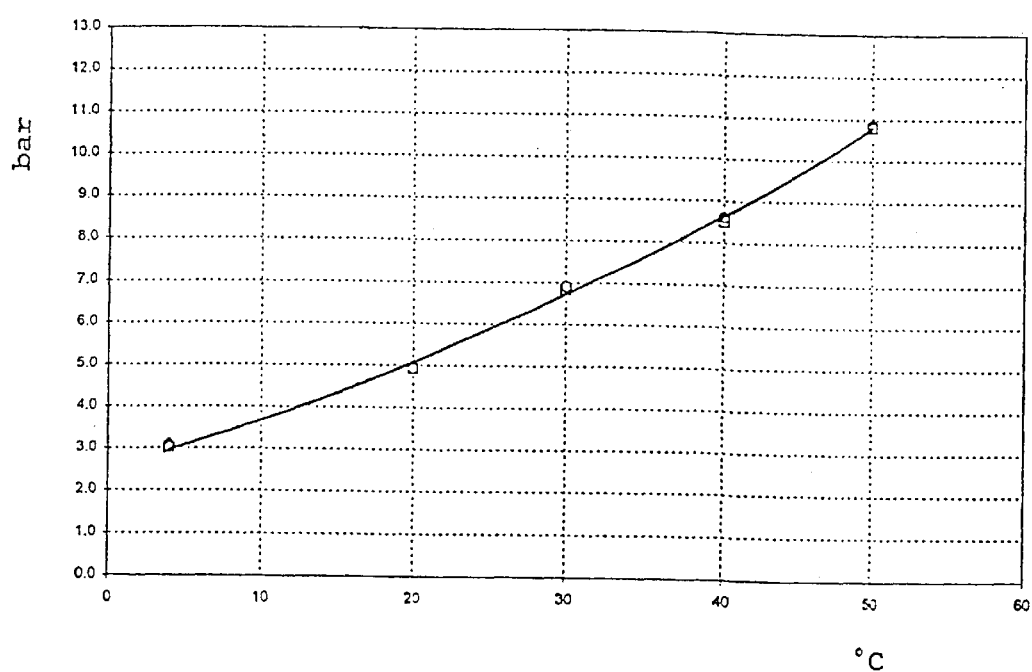
Figure 5A:
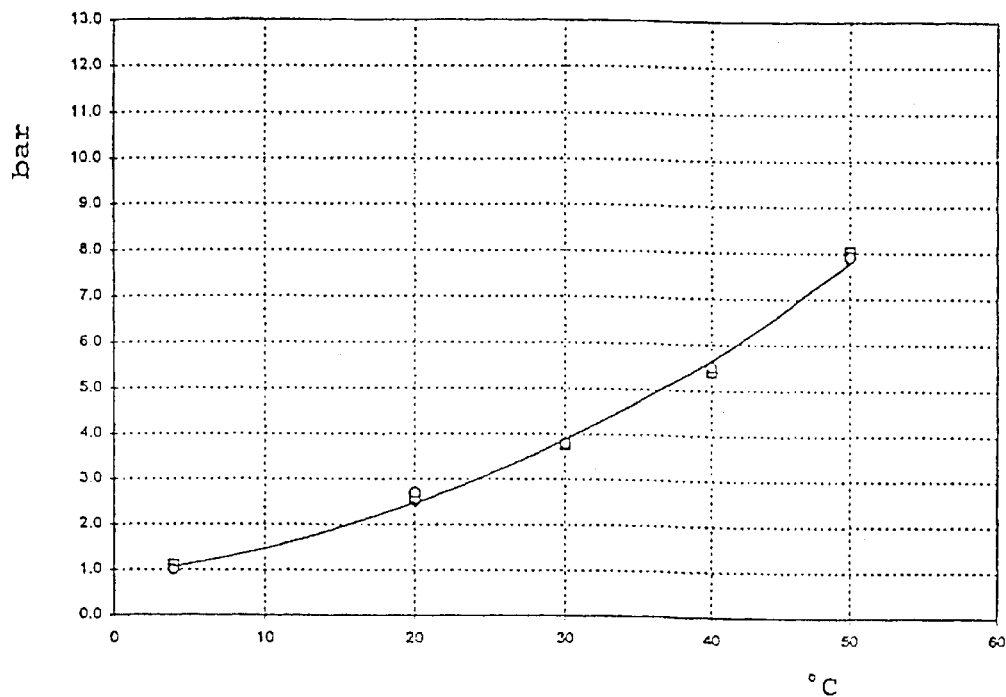
Figure 5B:
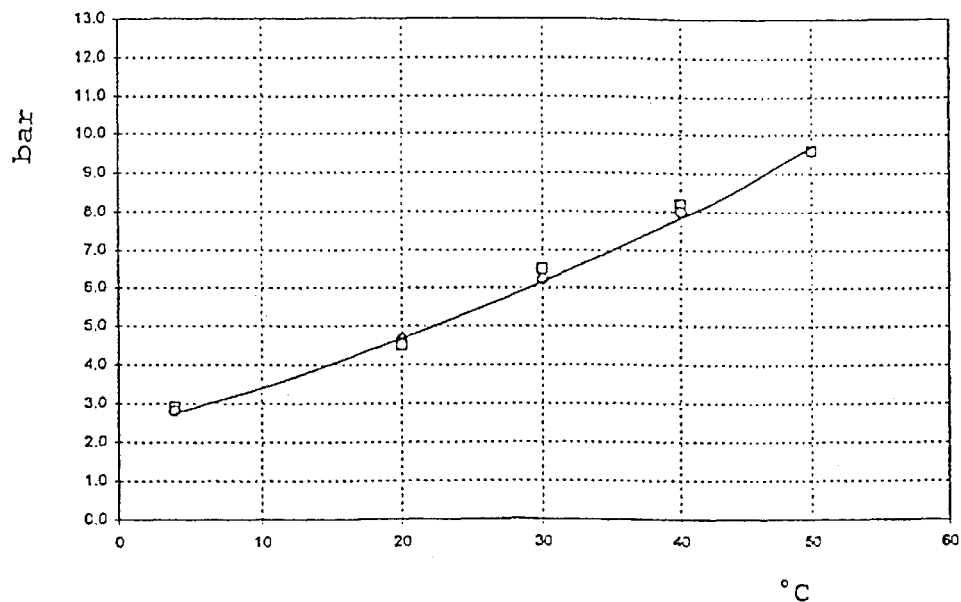
Figure 6A:
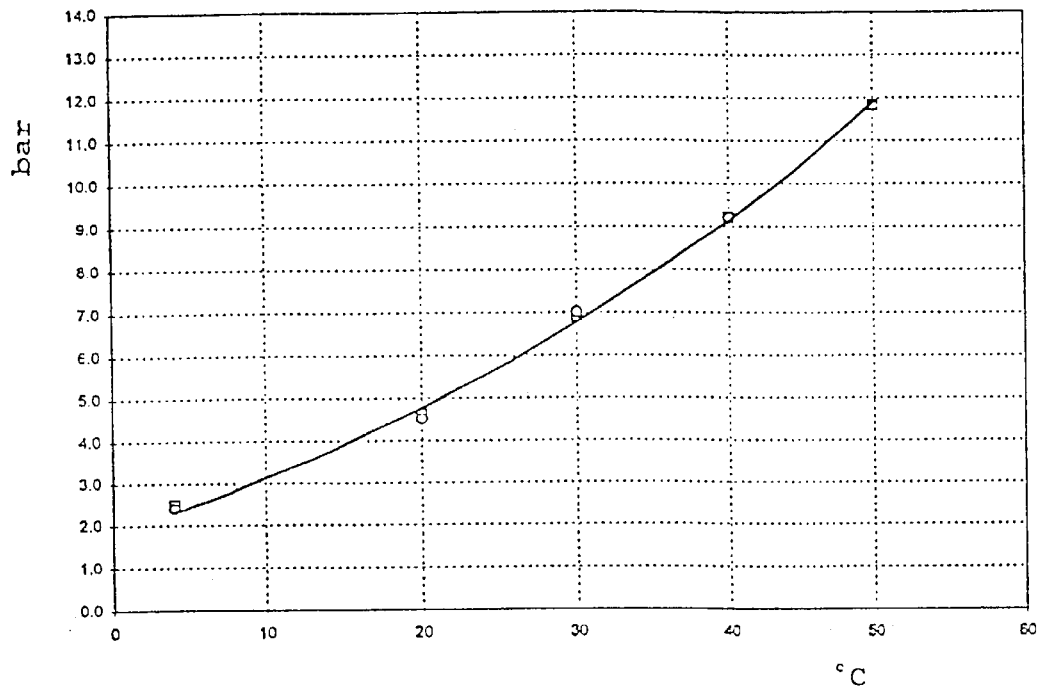
Figure 6B:
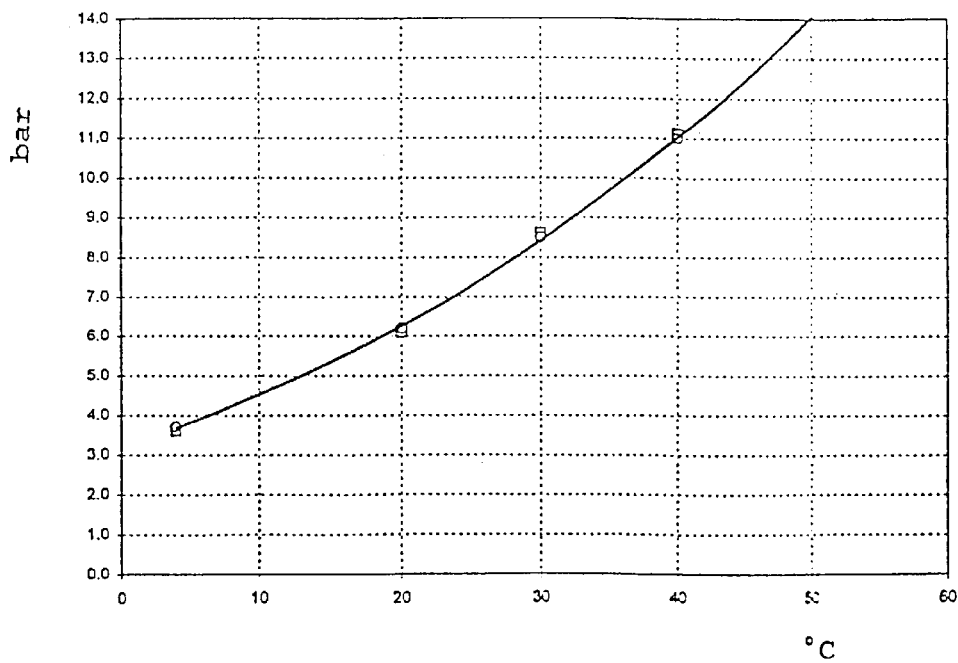

This application is a 371 of PCT/CH98/00037, filed Feb. 2, 1998.

FIELD OF THE INVENTION

The present invention relates to a pressure-liquefied propellant mixture based on hydrofluoroalkanes, to a medicinal aerosol formulation which contains such a propellant mixture, and to a process for the preparation of the aerosol formulation.

BACKGROUND OF THE INVENTION

Many gases, such as, for example, carbon dioxide and nitrogen, can admittedly be liquefied under pressure, but are not suitable as propellants for metered aerosols because the internal pressure in the container decreases very considerably with increasing emptying. For these reasons, only those propellant gases which can be liquefied at room temperature and only lead to a slight decrease in the internal pressure when the contents are successively sprayed are suitable for medicinal metered aerosols. These include the propellant-type alkanes, such as, for example, propane, butane and isobutane, and also the chlorofluorocarbons (CFCs), such as, for example, trichlorofluoromethane (F11), dichlorodifluoromethane (F12) and 1,2-dichloro-1,1,2,2-tetrafluoroethane (F114).

For aerosol applications such as hairsprays, deodorant sprays and the like, occasionally combinations of propellants have also been proposed.

For example, WO-A-94/01511 discloses aerosol formulations formed from a compressed gas (nitrogen, carbon dioxide, compressed air, oxygen, xenon and/or argon), a liquefied hydrocarbon propellant, active compound and carrier, where the formulations can typically contain 0.05–2.5% by weight of nitrogen and 1.0–12.0% by weight of liquefied hydrocarbon propellant and preferably have a content of 80–95% by weight of volatile carrier compounds, such as ethanol, propanol, pentane, water, acetone and the like. In the Derwent Abstract AN 86-228980, a dermatophytic agent is furthermore described, which contains 0.1–2% by weight of tolunaphthate, 0.5–70% by weight of propellant and 30–80% by weight of fluorinated alkyl halide (trichloromonofluoromethane, tetrachlorodifluoroethane, trichlorotrifluoroethane and/or dibromotetrafluoroethane) having a boiling point of at least 20° C. as a solvent; as a propellant, petroleum gas, dimethyl ether, dichlordifluoromethane, dichlorotetrafluoroethane, carbon dioxide etc. should be suitable. On the other hand, WO-A-93/17665 discloses a method for the administration of physiologically active compounds, in which a supercritical liquid solution is formed from a supercritical liquid solvent and the active compound and this is then moved into the subcritical range. As supercritical solvents, carbon dioxide, dinitrogen monoxide, chlorofluorocarbons, xenon, sulphur hexafluoride, ethanol, acetone, propane and/or water should be suitable.

On account of the ozone problem, caused by the removal of free-radical chlorine atoms from the CFCs, many countries came to an understanding in the Montreal Agreement no longer to use the CFCs as propellants in future. Suitable CFC substitutes for the medicinal area are fluorinated alkanes, especially 1,1,1,2-tetrafluoroethane (HFA 134a) and 1,1,1,2,3,3,3-heptafluoropropane (HFA 227), since these are inert and have a very low toxicity. On account of their physical properties, such as pressure, density, etc., they are particularly suitable to replace the CFCs such as F11, F12 and F114 as propellants in metered aerosols.

U.S. Pat. No. 4,139,607 furthermore proposed a propellant system formed from liquefied bis(difluoromethyl) ether and gaseous carbon dioxide, which unlike combinations of carbon dioxide with other known propellants such as trichlorofluoromethane or methylene chloride should produce satisfactory aerosol patterns, but which has not been successful. According to the disclosure of U.S. Pat. No. 4,139,607, other, conventional propellants such as dinitrogen monoxide, hydrocarbons and fluorocarbons or liquid carriers, such as ethanol, perchloroethylene, trichloroethylene, acetone, amyl acetate, water and the like, can be added to the propellant system, ethanol and bis (difluoromethyl) ether in the weight ratio of approximately 1:1 usually being used in the examples disclosed. On the other hand, it is stated in the Derwent Abstract AN 89-184245 that hydrocarbons, such as butanes and pentanes, other compressed gases, such as carbon dioxide, dimethyl ether, nitrogen and dinitrogen oxide, or fluorocarbons could also be used instead of CFCs in aerosol pressure packs for the administration of medicaments.

CFC-free medicinal aerosol preparations containing HFA 134a are already encompassed by the general teaching of U.S. Pat. No. 2,868,691 and U.S. Pat. No. 3,014,844 and disclosed in DE-A-2 736 500 and EP-A-0 372 777. Examples containing HFA 227 are found in WO-A-91/11495, EP-A-0 504 112 and EP-B-0 550 031. It is known from various publications that the customary auxiliaries used in CFC-containing metered aerosols, such as, for example, lecithin, sorbitan trioleate and oleic acid, only dissolve inadequately in hydrofluoro-alkanes (in the context of the present invention designated by "HFA"), such as, for example HFA 134a and HFA 227, because chain lengthening and the substitution of the chlorine atoms by fluorine atoms leads to a worsening of the solubility properties for polar substances. Even in the case of the CFCs, which in comparison to the HFAs are considerably better solvents, ethanol or other cosolvents were often added to improve the solubility in order to be able to administer pharmaceuticals such as, for example, isoprenaline and epinephrine (cf. U.S. Pat. No. 2,868,691) as an aerosol. It was therefore obvious to improve not only the solubility of the CFCs, but also that of the HFAs, by addition of ethanol. Examples of this are found in the specialized literature and in various patent applications. Alternatively to this, there are a number of developments of aerosol preparations containing HFA 134a and/or HFA 227 liquefied under pressure, which use propellant-soluble auxiliaries, such as, for example, fluorinated surface-active substances (WO-A-91/04 011), mono- or diacetylated glycerides (EP-A-0 504 112) or polyethoxylated compounds (WO-A-92/00 061), which can dissolve in the two propellants in the necessary amount without addition of ethanol. Hitherto, however, only one product based on HFAs has been permitted as a bioequivalent substitute, namely a suspension aerosol formulation of salbutamol sulphate in HFA 134a, ethanol and oleic acid (Airomir®, 3M Health Care Ltd., England).

OBJECTS OF THE INVENTION

For new developments of medicinal, CFC-free aerosol preparations, hydrofluoroalkanes such as HFA 134a (vapour pressure about 6 bar at 20° C.) and HFA 227 (vapour pressure about 4.2 bar at 20° C.) are preferably used today as propellants. Both propellants differ with respect to their density (about 1.4 mg/ml for HFA 227 and 1.2 mg/ml for HFA 134a at 20° C.), which is important, in particular for suspensions. If the active compound has a higher density than the propellant, sedimentation occurs, if its density is lower, flotation occurs. It therefore suggests itself under certain circumstances to use propellant mixtures to solve the problem and/or to add cosolvents such as ethanol, diethyl ether or other low-boiling solvents or propellants such as n-butane to lower the density. An important disadvantage of the HFAs is their low dissolving power in comparison to the CFCs, in particular in comparison to F11. The solvent properties decrease with increasing chain length in the sequence F11>HFA 134a>HFA 227. For this reason, without increasing the hydrophilicity by addition of polar solvents, such as, for example, ethanol, the suspending auxiliaries customarily used in CFCs, such as sorbitan trioleate, lecithin and oleic acid, can no longer be dissolved and thus used in the customary concentrations (about 1:2 to 1:20, based on the active compound).

It is generally known that in the case of suspension formulations only active compound particles which are smaller than 6 $\mu$m are respirable. For the desired deposition thereof in the lungs, these must therefore be comminuted before processing by means of special procedures, such as, for example, micronization (grinding). In the case of most active compounds, the grinding process leads to an increase in surface area, which is usually accompanied by an increase in the electrostatic charge. This can lead to agglomeration or coagulation in the aerosol preparation and, in general, complicates homogeneous active compound dispersion. As a result of the interfacial and charge activities, there is frequently an adsorption of active compound at interfaces, which leads, for example, to ring formation in the container at the site where the liquid phase changes into the gas phase. In addition, the suspensions can often only be inadequately stabilized or kept in the dispersed state, which can also be linked with a change in the dose per puff if before use, i.e. before inhalation, the suspension cannot be homogeneously redispersed by shaking. The imperfect wetting or dispersion of the active compound particles also results in these in many cases having a high adsorption tendency and adhering to surfaces, such as, for example, the container inner wall or the valve, which then leads to a putative underdosage and to poor dosage accuracy in the spray burst or the content uniformity (CU) of the declared number of, for example, 200 or 300 spray bursts (i.e. individual doses). In the case of suspensions, as a rule it is therefore necessary to add a surface-active auxiliary or a lubricant, because otherwise jamming of the valves and an inaccurate delivery of the active compound from spray burst to spray burst can occur. Particularly problematical is a change or reduction of the inhalable, respirable particles, of the so-called "fine particle fraction" (FPF), occurring during storage, which leads to a decrease in the activity of the HFA preparation.

SUMMARY OF THE INVENTION

To overcome the problems presented above, it is possible, for example by pharmaceutical technology measures, to change the wetting and solubility properties of the active compound. As a rule, however, surface-active substances are added, such as were already used earlier in the CFC-containing formulations. Because, however, surface-active agents such as oleic acid and lecithin only dissolve inadequately in hydrofluoroalkanes such as HFA 134a and/or HFA 227, a cosolvent such as ethanol is usually added in order that the pharmaceutical technology problems can be better controlled.

If higher ethanol concentrations are added, the density of the propellant mixture is lowered which, especially in the case of suspensions, can lead to undesired active compound sedimentation. In addition, however, as a result of the increase in solubility, partial dissolution effects can occur during storage, which then lead to crystal growth. This effect as well as an agglomeration of the active compound particles can then lead in the course of storage to a change or lowering of the inhalable, respirable particles, the so-called "fine particle fraction" (FPF).

To measure the aerodynamic particle size distribution and the fraction, the mass or the dose of the inhalable, respirable particles (i.e. the fine particle fraction FPF, fine particle mass FPM or fine particle dose FPD), impacters such as, for example, the 5-stage multistage liquid impinger (MSLI) or the 8-stage Andersen cascade impacter (ACI), which are described in chapter 601 of the United States Pharmacopoeia (USP) or in the Inhalants Monograph of the European Pharmacopoeia (Ph. Eur.), are suitable.

With the aid of the aerodynamic particle size distribution, it is possible by means of a "log-probability plot" (logarithmic presentation of the probability distribution) to estimate the mass median aerodynamic diameter (MMAD) of aerosol preparations and deduce whether the active compound is deposited more easily in the upper or lower lung region.

If the active compound is present in the HFA propellant gas/ethanol mixture not in suspended form, but dissolved form, problems with respect to the scattering of the dosage accuracy per puff are usually less pronounced.

With the same ethanol content, a larger percentage of inhalable (smaller) particles are obtained with HFA 134a in comparison with HFA 227, which is to be attributed to the higher pressure of HFA 134a. In principle: the higher the internal pressure in the aerosol container, the finer the particle spectrum of the aerosol cloud. Solution aerosols containing a low proportion of ethanol as a rule have a smaller MMAD (0.8–1.5 μm) when using fine atomizing nozzles than suspension aerosols (2–6 μm). This is connected with the fact that droplets are produced in solution aerosols and particles in suspension aerosols.

For the topical application of active compounds in the area of the bronchi and bronchioles, particle sizes of about 2–4 μm are advantageous, such as are customarily achieved with suspension formulations. Smaller particles which reach the alveolar area are partly exhaled (<0.5 μm) or reach the systemic circulation as a result of absorption. It follows from this that aerosol preparations for systemic application favourably should have particle sizes of about 0.5 μm–2 μm, where, for example, a monodisperse aerosol having a very high proportion of particles in the range of about 1 μm would be particularly advantageous. Depending on the desired deposition site, a smaller or larger MMAD and optionally a monodisperse distribution spectrum is therefore preferred. With respect to the aerodynamics: the greater the mass of the particles the larger their tendency to continue flying in a straight line. It results from this that in the case of a change in the flow direction impaction of particles occurs. It is known from deposition studies that even with an optimal inhalation manoeuvre only about 20% of the particles emitted from a metered aerosol reach the lungs and almost 80% impact in the oropharynx.

In the case of ethanol-containing solution aerosols, unfortunately problems often occur relating to the active compound stability. The degree of decomposition of active compound, such as, for example, budesonide, fenoterol HBr, formoterol fumarate, ipratropium bromide, salbutamol, etc., can be above the tolerated highest values (<0.5%) after storage in ethanol-containing solution aerosols. It is additionally disadvantageous that at higher ethanol concentrations of, for example, 10%–30% the proportion of inhalable particles (<6 μm) decreases, because as a result of the different evaporation characteristics of ethanol less energy is provided for the dispersion of the aerosol preparation, i.e. for the formation of inhalable droplets or particles. These and other reasons indicate why most metered aerosols have been brought onto the market as suspensions.

On account of the relationships presented above, it would thus be desirable for metered aerosols to have a propellant system with which:

- active compounds can be better wetted;
- suspension aerosols having improved suspension and shelf life properties can be prepared;
- solution aerosols having improved storage stability and lower ethanol addition can be prepared;
- the dosage accuracy can be improved;
- the particle sizes or the particle size distribution spectrum can be better adjusted; and
- the fine particle dose can be increased.

This object is achieved according to the invention by use of a propellant mixture based on carbon dioxide and at least one hydrofluoroalkane having 1 to 3 carbon atoms.

It has namely been found that carbon dioxide dissolves in the hydrofluoroalkanes and virtually loses its properties as a compressible gas. With increasing emptying, hydrofluoroalkane/carbon dioxide propellant mixtures of this type show only a slight decrease of the internal pressure in the container, which makes possible their use as propellants for metered aerosols. As a result of the addition of carbon dioxide to the hydrofluoroalkanes, the pressure increases approximately linearly with increasing carbon dioxide concentration. Furthermore, the pressure course as a function of the temperature is affected by the content of carbon dioxide to the effect that unlike pure hydrofluoroalkanes (cf. FIG. 2 of EP-B-0 550 031) only a weakly exponential, nearly linear pressure rise occurs if the temperature is increased stepwise, for example, from 20° C. to 50° C. These effects are also observed if the propellant mixture additionally contains a cosolvent.

BRIEF DESCRIPTION OF THE DRAWINGS

FIGS. 1–6 show graphic presentations of the pressure course as a function of the temperature for examples of propellant mixtures according to the invention, namely FIGS. 1*a* and 1*b* for a propellant mixture of 300 parts by weight of HFA 134a and 1 or 3 parts by weight of carbon dioxide, FIGS. 2*a* and 2b for a propellant mixture of 210 parts by weight of HFA 134a, 90 parts by weight of ethanol and 1 or 3 parts by weight of carbon dioxide, FIGS. 3*a* and 3*b* for a propellant mixture of 300 parts by weight of HFA 227 and 1 or 3 parts by weight of carbon dioxide, FIGS. 4*a* and 4*b* for a propellant mixture of 277.5 parts by weight of HFA 227, 22.5 parts by weight of ethanol and 1 or 3 parts by weight of carbon dioxide, FIGS. 5*a* and 5*b* for a propellant mixture of 210 parts by weight of HFA 227, 90 parts by weight of ethanol and 1 or 3 parts by weight of carbon dioxide, and FIGS. 6*a* and 6*b* for a propellant mixture of 180 parts by weight of HFA 134a, 120 parts by weight of HFA 227 and 1 or 3 parts by weight of carbon dioxide.

DETAILED DESCRIPTION

Since the propellant pressure of $CO_2$-containing hydrofluoroalkanes does not increase quadratically, but only approximately linearly, propellant systems of this type are therefore far less temperature-dependant than, for example, pure CFC mixtures or hydrofluoroalkanes such as HFA 134a and/or HFA 227

Surprisingly, it was additionally found that the addition of carbon dioxide to hydrofluoroalkanes such as HFA 134a and/or HFA 227 leads to a significant improvement in the wetting properties for pharmaceutically active compounds. By passing in carbon dioxide, hydrofluoroalkanes are thus similarly altered in their wetting properties to an active compound coating to the effect that the formulation problems existing with HFA 134a, HFA 227 and other hydrofluoroalkanes can be overcome in relation to suspension aerosols as well as solution aerosols. Even an addition of carbon dioxide in an order of magnitude of 0.2% by weight or less significantly reduces the adhesion tendency of active compounds to interfaces and decreases their adsorption, agglomeration and coagulation. Even as a result of addition of small amounts of carbon dioxide, the hydrofluoroalkanes are rendered hydrophilic to a certain extent. Suspensions which are distinguished by controlled flocculation can thus be prepared from many active compounds without further auxiliaries. As a result of the better suspending properties, in many cases addition of partly undesirable surface-active suspending agents such as, for example, oleic acid or of a cosolvent such as, for example, ethanol can be dispensed with.

The propellant mixture according to the invention, however, also offers advantages in aerosol formulations in which a surface-active agent and/or a cosolvent is necessary or desired. On the one hand, the use of the carbon dioxide-containing propellants namely often allows a reduction in the amount of cosolvent needed and a better solubility of conventional surface-active agents. On the other hand, the disadvantageous effect of cosolvents such as ethanol on the droplet size can be avoided completely or to the greatest extent, since by means of appropriate increase in the carbon dioxide concentration, the internal pressure can be adjusted even at comparatively high cosolvent concentrations such that an adequate fine particle dose can be achieved.

With the aid of carbon dioxide, it is also possible to displace oxygen from the hydrofluoroalkanes, whereby the storage stability of oxidation-sensitive active compounds is improved. Moreover, using carbon dioxide the internal pressure in the aerosol container can be adjusted such that in comparison to a conventional CFC or HFA metered aerosol the FPF and the MMAD can be virtually affected as appears to be most efficient for use. It is thus possible to produce MDIs (metered dose inhalers) for local as well as topical application. In particular for systemic administration, completely new possibilities of use are opened up, because in combination with suitable atomizing nozzles it is possible to prepare virtually monodisperse aerosols with a defined MMAD and high respirable fractions.

The invention therefore relates to a pressure-liquefied propellant mixture for aerosols, comprising carbon dioxide and a hydrofluoroalkane of the general formula $$C_xH_yF_z \quad (I)$$

in which x is the number 1, 2 or 3, y and z are each an integer ≧1 and y+z=2x+2.

The preparation of the propellant mixtures according to the invention can be carried out in a known manner by passing carbon dioxide under pressure into a hydrofluoroalkane of the formula I.

The propellant mixture according to the invention is fundamentally suitable for any desired aerosol uses such as, for example, cosmetic and household sprays. On account of the advantages described—such as smaller decrease in the internal pressure on emptying, lower temperature dependence and easier adjustability of the internal pressure, improved wetting properties for pharmaceutically active compounds and usability of conventional surface-active agents such as oleic acid, lecithin and sorbitan trioleate—the propellant mixture according to the invention, however, is especially also suitable for medicinal aerosol formulations and in particular for inhalation aerosols.

The invention therefore also relates to a medicinal aerosol formulation, comprising an effective amount of a pharmaceutically active compound and a pressure-liquefied propellant mixture as defined above.

Examples of suitable hydrofluoroalkanes which can be used in the propellant mixtures and aerosol formulations according to the invention are: difluoromethane (HFA 32), pentafluoroethane (HFA 125), 1,1,2,2-tetrafluoroethane (HFA 134), 1,1,1,2-tetrafluoroethane (HFA 134a), 1,1,2-trifluoroethane (HFA 143), 1,1,1-trifluoroethane (HFA 143a), 1,1-difluoroethane (HFA 152a), 1,1,1,2,3,3,3-heptafluoropropane (HFA 227), hexafluoropropane (HFA 236), pentafluoropropane (HFA 245) and the like. In general, hydrofluoroalkanes having 2 or 3 carbon atoms are preferred. Particularly preferred propellant mixtures and aerosol formulations are those which contain 1,1,1,2-tetrafluoroethane (HFA 134a), 1,1,1,2,3,3,3-heptafluoropropane (HFA 227) or a mixture of the two, for example a 1:1 mixture.

The carbon dioxide content of the propellant mixtures and aerosol formulations according to the invention can preferably be approximately 0.0001 to 10% by weight, as a rule concentrations of up to approximately 6% by weight, in particular up to approximately 3% by weight, being particularly preferred. In most cases, a carbon dioxide concentration of at least approximately 0.01% by weight, preferably at least approximately 0.1% by weight, is indicated. In the case of medicinal aerosols and in particular in the case of inhalation aerosols, in general a carbon dioxide content of approximately 0.01 to 2% by weight, typically approximately 0.1 to 1.0% by weight, is preferred; as a rule higher concentrations are only indicated if the formulation contains a comparatively high proportion of cosolvents such as ethanol or water.

Suitable pharmaceutically active compounds for the aerosol formulations according to the invention are fundamentally all active compounds which can be administered as aerosols, such as beta-mimetics, corticosteroids, anticholinergics, cyclooxygenase, mast cell, lipoxygenase and proteolytic enzyme inhibitors, arachidonic acid, leukotriene, thromboxane, sodium/potassium channel, neurokinin, tachykinin, bradykinin, muscarine, histamine, phosphodiesterase and selectin antagonists, potassium channel blockers, anti-infective agents, antibiotics, pentamidine, cytostatics, fungi-statics, free-radical scavengers, vitamins, hormones, immunostimulants, immunosuppressants, mucolytics, heparin, antidiabetics, analgesics, soporifics and the like, for example beta-mimetics such as salbutamol, formoterol, salmeterol, fenoterol, clenbuterol, terbutaline, bambuterol, broxaterol, epinephrine, isoprenaline, orciprenaline, hexoprenaline, tulobuterol, reproterol, bamethan etc., corticoids such as beclomethasone, betamethasone, ciclomethasone, dexamethasone, triamcinolone, budesonide, butixocort, ciclesonide, fluticasone, flunisolide, icomethasone, mometasone, tixocortol, loteprednol etc., anticholinergics and spasmolytics such as atropine, scopolamine, N-butylscopolamine, trospium chloride, ipratropium bromide, oxitropium bromide, thiotropium bromide, drofenine, oxybutinine, moxaverine, glycopyrrolate etc., mast cell inhibitors such as cromoglycic acid, nedocromil etc. and lipoxygenase inhibitors such as zileuton, leukotriene antagonists such as iralukast, zafirlukast and pranlukast, sodium channel antagonists such as amiloride, potassium channel antagonists such as bimakalim, arachidonic acid antagonists such as 2-benzoxazolamine, histamine receptor antagonists such as epinastine, cetrizine, mizolastine and mequitamium, antimigraine agents such as ergot alkaloids, methysergide, ergotamine, serotonin, sumatriptan, zolmitriptan, cyclandelate etc., analgesics such as fentanyl, morphine, buprenorphine, opium, heroin, nalbuphine, pentazocine, oxycodone, tramadol, pethidine, tilidine, methadone, nefopam, dextropropoxyphene, piritramide etc., mucolytics such as RNase, acetylcysteine, ambroxol, apafant, bromhexine, surfactant etc., antiemetics such as bromopride, domperidone, metoclopramide, triethylperazine, trifluoropromazine, meclozine, chlorphenoxamine, dimenhydrinate etc., antibiotics such as penicillins (e.g. azlocillin), cephalosporins (e.g. cefotiam or ceftriaxone), carbapenems, monobatams, aminoglycosides (e.g. streptomycin, neomycin, gentamycin, amikacin or tobramycin), quinolones (e.g. ciprofloxacin), macrolides (e.g. erythromycin), nitroimidazoles (e.g. tinidazole), lincosamides (e.g. clindamycin), glycopeptides (e.g. vancomycin), polypeptides (e.g. bacitracin) etc., vitamins and free-radical scavengers such as vitamin A, B, C, D or E, catalase, superoxide dismutase, reduced glutathione etc., antidiabetics such as glibenclamide, glipizide, gliclazide, glimepiride, troglitazone etc., soporifics such as benzodiazepines, piperidonediones, antihistaminics etc., neuroleptics, antidepressants and anticonvulsants such as benzodiazepines, phenothiazines, butyrophenones, sulpiride, hydantoins, barbiturates, succinimides, carbamazepine etc., hormones such as androgens (e.g. testosterone), antioestrogens, oestrogens (e.g. oestradiol), gestagens (e.g. progesterone), corticosteroids, calcitonin, parathyrin, somatotropin, oxytocin, prolactin, glucagon, erythropoietin, atriopeptin, melanotropin, thyrotropin, gonadotropin, vasopressin, insulin etc., potency agents such as alprostadil, cytostatics such as nitrogen mustard derivatives (e.g. ifosphamide), N-nitrosourea derivatives (e.g. lomustine), antagonists of purine and pyrimidine bases (e.g. fluorouracil), platinum complexes (e.g. carboplatin), anthracyclines (e.g. doxorubicin), podophylline derivatives (podophyllotoxin).

The active compounds mentioned can optionally be used in the form of their isomers, enantiomers or racemates and, in the case of acids or bases, as such or in the form of their pharmaceutically acceptable salts. The optimum amount of active compound in the formulations according to the invention depends on the particular active compound. As a rule, however, aerosol formulations are preferred which contain at least approximately 0.0001 and at most approximately 5% by weight, in particular approximately 0.01 to 3% by weight, of active compound.

The aerosol formulations according to the invention can be prepared in a manner known per se by passing carbon dioxide under pressure into a liquefied hydrofluoroalkane of the formula I and adding the pharmaceutically active compound. The carbon dioxide and the active compound can fundamentally be added in any desired sequence. In the case of suspension formulations, however, as a rule it is preferred first to pass in the carbon dioxide into the propellant and then to add the micronized active compound. The micronization of the active compound can be carried out in a manner known per se and is preferably carried out such that a particle size of approximately 0.5 to 6 $\mu$m is obtained.

The propellant mixtures and aerosol formulations according to the invention can contain one or more hydrofluoroalkanes and, if desired, further propellants. Preferably, however, they contain no chlorofluorocarbons. In general, those propellant mixtures and aerosol formulations are particularly preferred which—apart from compounds which can be used, if desired, as cosolvents, such as water, lower alkanes, lower alcohols and lower ethers—contain only carbon dioxide and one or more hydrofluoroalkanes of the formula I as propellants. The hydrofluoroalkane or the hydrofluoroalkanes and the carbon dioxide concentration are preferably selected such that an internal pressure of approximately 3 to 12 bar, particularly preferably approximately 4 to 7 bar, can be established in the aerosol container at 20° C.

The aerosol formulations according to the invention are suitable for suspension and solution formulations, and they can contain customary additives such as cosolvents and surface-active agents. The active compound and optionally further additives can be added in a manner known per se. As a result of the improvement in the fine particle fraction achievable according to the invention and the high respirable fractions of up to 70% achievable thereby, it is frequently possible to decrease the active compound concentration by up to approximately 50%.

The use of a cosolvent is frequently indicated, in particular with solution formulations, but can occasionally also be advantageous with suspension formulations. Suitable cosolvents are, in particular, water, lower alcohols, lower alkanes and lower ethers, preferably water, alcohols having 1 to 3 carbon atoms, alkanes having 3 to 6 carbon atoms and dialkyl ethers having 2 to 4 carbon atoms, such as water, ethanol, propanol, ethylene glycol, propylene glycol, propane, butane, isobutane, pentane, dimethyl ether, diethyl ether and the like. Ethanol is particularly preferred. If present, the proportion of cosolvent in the propellant mixtures and aerosol formulations according to the invention can in general be approximately 0.1 to 50% by weight, in particular approximately 1 to 30% by weight, based on the total mixture or the total formulation. In most cases, (if cosolvent is necessary or desired), a cosolvent concentration of approximately 0.1 to 30% by weight, typically approximately 0.1 to 10% by weight, is sufficient.

The proportion of one or more hydrofluoroalkanes of the formula I in the propellant mixtures and aerosol formulations according to the invention can accordingly in general be at least approximately 40% by weight, preferably at least approximately 64% by weight and particularly preferably at least approximately 87% by weight of the total mixture or of the total formulation. In the case of the medicinal aerosol formulations, however, the proportion of hydrofluoroalkanes with respect to the content of active compound, surface-active agent and possible further additives can also be lower and can be, for example, at least approximately 29% by weight.

In particular, the use of a surface-active agent is frequently indicated with suspension formulations, but can also be advantageous with solution formulations, e.g. for valve lubrication. Fundamentally, all customary surface-active agents such as oleic acid, sorbitan trioleate, cetylpyridinium chloride, soya lecithin, polyoxyethylene(20) sorbitan monolaurate, polyoxyethylene(10) stearyl ether, polyoxyethylene(2) oleyl ether, polyoxyethylene(20) sorbitan monostearate, polyoxyethylene(20) sorbitan monooleate, polyoxypropylene-polyoxyethylene block co-polymers, polyoxypropylene-polyoxyethylene-ethylenediamine block copolymers, ethoxylated castor oil and the like are suitable. In general, oleic acid, sorbitan trioleate and lecithin are preferred. If present, the proportion of surface-active agent can in general be approximately 0.001 to 5% by weight, preferably approximately 0.01 to 1% by weight, based on the total formulation. Owing to the improved wetting properties of the propellant mixture according to the invention, however, often even concentrations of approximately 0.1% by weight or less are adequate.

If desired, the aerosol formulation according to the invention can furthermore contain water, for example in an amount from 0.0001 to 20% by weight, based on the total formulation, which can be advantageous in the case of certain active compounds.

The aerosol formulations according to the invention can furthermore contain, if desired, buffer substances or stabilizers such as citric acid, EDTA, vitamin E and the like. In general, substances of this type, if present, are used in amounts of not more than approximately 1% by weight, for example approximately 0.0001 to 1% by weight, based on the total formulation.

Using the propellant system according to the invention, it is possible to produce, for example, a beclomethasone metered aerosol which in comparison to a CFC-containing commercial product (Becotide®, Glaxo Pharmaceuticals, Great Britain) has a far better dosage accuracy and about 2.7 times as high an FPF. Complementary thereto, the deposition in the mouth tube is approximately halved and that in the "sample induction port" (artificial oropharynx) is reduced from about 50% to 20%. The beclomethasone formulation according to the invention thus makes it possible to design the metered aerosol more advantageously in relation to several aspects, since an increase in the respiratory dose with simultaneous reduction of the loss of active compound in the mouth tube, and a reduction in the oropharyngeal deposition, virtually makes possible a significant efficiency increase compared to the commercial product Becotide.

It is also possible using the present invention to administer, for example, antimigraine agents systemically by inhalation. Migraine patients who very frequently suffer from vomiting can thus be alternatively treated. Using the formulations for metered aerosols according to the invention, it is thus possible to provide active compounds or compound combinations as aerosols having defined properties. In comparison to commercial products, the particle size distribution spectrum can be adjusted such that the active compound can virtually be deposited in a targeted manner at the desired site in the lung in the form of "drug targeting". Using this type of optimized active compound administration, undesired concomitant effects can simultaneously be reduced.

Moreover, active compounds which were or have not been administered to the lungs and cannot be orally administered, since perorally they have a poor bioavailability and/or an undesired side effect spectrum, can be administered systemically by means of inhalation, which opens up completely new treatment possibilities. The invention of this "pulmonary drug targeting system" (PDTS) is illustrated further in the working examples by means of some formulation examples.

The aerosol formulations according to the invention can be sealed into customary pressure-tight containers with customary commercial metering valves with volumes of 25 μl to 100 μl and atomized using suitable customary commercial mouth tube adapters.

The invention is illustrated further by the following examples. The homogenization of active compound suspensions was carried out in each case using a rotor-stator homogenizer (Kinematika).

EXAMPLE 1 a) 2.5 g of beclomethasone dipropionate are weighed into a pressure addition vessel and dissolved with stirring in 55 g of ethanol, in which 0.25 g of oleic acid has been previously dissolved. After sealing and evacuation thereof, 1.5 kg of HFA 227, which has previously been aerated with $CO_2$ and adjusted to a pressure of 6.5 bar (20° C.) in an other pressure vessel, are added with stirring. The solution obtained is dispensed into aluminium containers sealed with metered valves by means of the pressure-filling technique (units from Pamasol W. Maeder, Pfäffikon, Switzerland).

The formulation obtained was compared with the commercial products Becotide® 100 and Becotide® 200 (Glaxo Pharmaceuticals, Great Britain; batches Nos. 10072926 and 10073077, respectively) and Becloforte® (Glaxo AG, Schönbühl, Switzerland; batch No. 5H052) based on CFC propellants, several samples of which were purchased in a pharmacy and kept in a horizontal position at room temperature until measurement. The novel formulations were kept in different positions (valve downwards or upwards) at 25° C. and 60% relative humidity until measurement or previously stored for 6 months at 30° C. and 70% relative atmospheric humidity (30°/70% rh). To determine the content uniformity, in the case of the commercial products in each case the puff Nos. 5–9 and 196–200 (3 canisters each) and in the case of the novel formulation actuations Nos. 3 and 200 (10 canisters each) were measured. The aerodynamic particle size distribution and the fine particle fraction FPF or the fine particle dose FPD (stages 2–8) were determined using an 8-stage Andersen cascade impacter according to USP 23 using puff Nos. 11–30 and 178–197 (3 canisters each, manual actuation). In all cases, the beclomethasone dipropionate was determined by means of HPLC and UV measurement at 230 nm. The mass median aerodynamic diameter MMAD was calculated from the corresponding logarithmic presentations of the probability distribution. The values obtained (number of measurements in brackets) and the relative standard deviations (RSD) are summarized in Table 1.

TABLE 1

| Product | Becotide | | Becloforte | Example 1 | |
|---|---|---|---|---|---|
| Declared value per puff | 100 μg | 200 μg | 250 μg | 100 μg | 100 μg |
| Storage | not defined | not defined | not defined | no* | 6 months, 30°/70% rh |
| Mass/puff | 79.3 mg | 86.9 mg | 87.9 mg | 68.8 mg | 67.9 mg |
| RSD | 13.3% | 8.1% | 3.3% | 2.9% | 5.3% |
| (n) | (30) | (30) | (30) | (20) | (40) |
| Dose/puff | 107.8 μg | 221.5 μg | 279.5 μg | 97.7 μg | 102.9 μg |
| RSD | 23.9% | 6.3% | 12.8% | 4.1% | 13.4% |
| (n) | (30) | (30) | (30) | (20) | (40) |
| USP throat | 55.2 μg | 122.9 μg | 160.0 μg | 18.9 μg | 13.0 μg |
| FPD (n = 6) | 26.9 μg | 45.4 μg | 47.9 μg | 61.5 μg | 71.8 μg |
| MMAD | ≈3.2 μm | ≈3.2 μm | ≈3.2 μm | ≈1.3 μm | ≈1.3 μm |

* initial investigation b) In the same manner as in paragraph a), a solution aerosol formulation of beclomethasone dipropionate was prepared in HFA 227, ethanol and oleic acid, but the pressure was adjusted to 4.5 bar (20° C.) by passing in carbon dioxide, and the solution obtained was dispensed into aluminium containers sealed with metering valves by means of the pressure-filling technique.

EXAMPLE 2

2.25 g of micronized ipratropium bromide are weighed into a pressure addition vessel. After sealing and evacuation thereof, 10.5 kg of HFA 227 which has previously been aerated with $CO_2$ and adjusted to a pressure of 6 bar (20° C.) in another pressure addition vessel are added. After homogenization of this mixture, the suspension obtained is dispensed into aluminium containers sealed with metering valves by means of the pressure-filling technique.

EXAMPLE 3

2.25 g of micronized ipratropium bromide and 11.25 g of micronized salbutamol are weighed into a pressure addition vessel. After sealing and evacuation thereof, 10.5 kg of HFA 227 which has previously been aerated with $CO_2$ and adjusted to a pressure of 6.25 bar (20° C.) in another pressure addition vessel are added. After homogenization of this mixture, the suspension obtained is dispensed into aluminium containers sealed with metering valves by means of the pressure-filling technique.

EXAMPLE 4

2 g of fluticasone propionate and 0.02 g of δ-tocopherol are weighed into a pressure addition vessel. After sealing and evacuation of the addition vessel, 1.5 kg of HFA 134a which has previously been aerated with $CO_2$ and adjusted to a pressure of 4.5 bar (20° C.) in another pressure addition vessel are added with stirring. The suspension obtained is dispensed into aluminium containers sealed with metering valves by means of the pressure filling technique.

EXAMPLE 5

5.0 g of micronized budesonide are weighed into a pressure addition vessel. After sealing and evacuation thereof, a mixture of 0.85 kg of HFA 134a and 0.85 kg of HFA 227 which has previously been aerated with $CO_2$ and adjusted to a pressure of 6.5 bar (20° C.) in another pressure addition vessel is added. After homogenization of this mixture, the suspension obtained is dispensed into aluminium containers sealed with metering valves by means of the pressure-filling technique.

EXAMPLE 6

4.5 g of micronized oxitropium bromide and 0.675 g of micronized formoterol fumarate are weighed into a pressure addition vessel. After sealing and evacuation thereof, 10.5 kg of HFA 227 which has previously been aerated with $CO_2$ and adjusted to a pressure of 6.25 bar (20° C.) in another pressure addition vessel are added. After homogenization of this mixture, the suspension obtained is dispensed into aluminium containers sealed with metering valves by means of the pressure-filling technique.

EXAMPLE 7

112.5 g of micronized lomustine are weighed into a pressure addition vessel. After sealing and evacuation thereof, 10.5 kg of HFA 227 which have been aerated with $CO_2$ and adjusted to a pressure of 4.5 bar (20° C.) in another pressure addition vessel in which 312 g of ethanol have been initially introduced are added. After homogenization of this mixture, the formulation obtained is dispensed into aluminium containers sealed with metering valves by means of the pressure-filling technique.

EXAMPLE 8

5 g of heparin are weighed into a pressure addition vessel and suspended with stirring with 50 g of ethanol in which 0.25 g of lecithin have previously been dissolved. After sealing and evacuation thereof, 1.5 kg of HFA 227 which have previously been aerated with $CO_2$ and adjusted to a pressure of 4.5 bar (20° C.) in another pressure addition vessel are added with stirring and homogenized. The suspension obtained is dispensed into aluminium containers sealed with metering valves by means of the pressure-filling technique.

EXAMPLE 9

2.6 g of oestradiol are weighed -into a pressure addition vessel and dissolved with stirring in 405.6 g of ethanol in which 0.26 g of oleic acid has previously been dissolved. After sealing and evacuation thereof, 6.7 kg of HFA 134a which have previously been aerated with $CO_2$ and adjusted to a pressure of at most 6.5 bar (20° C.) in another pressure addition vessel are added with stirring. The formulation obtained is dispensed into aluminium containers sealed with metering valves by means of the pressure-filling technique.

EXAMPLE 10

2.6 g of fentanyl are weighed into a pressure addition vessel and dissolved with stirring in 405.6 g of ethanol in which 0.26 g of oleic acid has previously been dissolved. After sealing and evacuation thereof, 6.7 kg of HFA 134a which have previously been aerated with $CO_2$ and adjusted to a pressure of at most 6.5 bar (20° C.) in another pressure addition vessel are added with stirring. The formulation obtained is dispensed into aluminium containers sealed with metering valves by means of the pressure-filling technique.

EXAMPLE 11

2.6 g of scopolamine are weighed into a pressure addition vessel and dissolved with stirring in 405.6 g of ethanol in which 0.26 g of oleic acid has previously been dissolved. After sealing and evacuation thereof, 6.7 kg of HFA 134a which have previously been aerated with $CO_2$ and adjusted to a pressure of 8 bar (20° C.) in another pressure addition vessel are added with stirring. The solution obtained is dispensed into aluminium containers sealed with metering valves by means of the pressure-filling technique.

EXAMPLE 12

2.6 g of sumatriptan are weighed into a pressure addition vessel and dissolved with stirring in 405.6 g of ethanol in which 0.26 g of oleic acid has previously been dissolved. After closing and evacuation thereof, 6.7 kg of HFA 134a which have previously been aerated with $CO_2$ and adjusted to a pressure of 7 bar (20° C.) in another pressure addition vessel are added with stirring. The preparation obtained is dispensed into aluminium containers sealed with metering valves by means of the pressure-filling technique.

EXAMPLE 13

15.6 g of beclomethasone dipropionate are dissolved in 811 g of ethanol which contains 3 g of oleic acid. The clear solution is mixed with 7.3 kg of HFA 227. The mixture obtained is added to 9.4 g of initially introduced salbutamol sulphate and adequately homogenized. After conclusion of the homogenization, the mixture is diluted with 2 kg of HFA 227 which have been aerated with $CO_2$ and adjusted to a pressure of 5 bar (20° C.), diluted and finally homogenized. The finished preparation is dispensed into aluminium containers sealed with metering valves by means of the pressure-filling technique.

EXAMPLE 14

20 g of triamcinolone acetonide are dissolved in 1.5 kg of ethanol. The solution is dispensed into open aluminium containers and these are sealed with suitable metering valves. The containers are filled by means of the pressure-filling technique with a total of 4 kg of HFA 227 which have been aerated with $CO_2$ and adjusted to a pressure of 5 bar (20° C.).

What is claimed is:

1. An inhalable medicinal aerosol formulation comprising an effective amount of a pharmaceutically active compound and a pressure-liquified homogeneous propellant mixture, comprising carbon dioxide and hydrofluoroalkane of formula $$C_xH_yF_z \qquad (I)$$

in which x is the number 1, 2 or 3, y and z are each an integer $\geq 1$ and y+z=2x+2,
the carbon dioxide being present in an amount of from 0.01 to 2% by weight, based on the total weight of the formulation, wherein the hydrofluoroalkane of the formula I is selected from the group consisting of 1,1,1,2-tetrafluoroethane; 1,1,1,2,3,3,3-heptafluoropropane; and 1,1,1,2-tetrafluoroethane in the presence of 1,1,1,2,3,3,3-heptafluoropropane, wherein the inhalable medicinal aerosol formulation is contained in a metered dose inhaler.

2. The aerosol formulation according to claim 1, wherein the hydrofluoroalkane of the formula I is present in an amount of at least 64% by weight, based on the total weight of the formulation.

3. The aerosol formulation according to claim 1, wherein the pharmaceutically active compound is a beta-mimetic selected from the group consisting of salbutamol, formoterol, salmeterol, fenoterol, clenbuterol, terbutaline, bambuterol, broxaterol, epinephrine, isoprenaline, orciprenaline, hexoprenaline, tulobuterol, reproterol, bamethan, and pharmaceutically acceptable salts thereof.

4. The aerosol formulation according to claim 1, wherein the pharmaceutically active compound is a corticoid selected from the group consisting of beclomethasone, betamethasone, ciclomethasone, dexamethasone, triamcinolone, budesonide, butixocort, ciclesonide, fluticasone, flunisolide, icomethasone, mometasone, tixocortol, loteprednol, and pharmaceutically acceptable salts thereof.

5. The aerosol formulation according to claim 1, further comprising a cosolvent selected from the group consisting of water, ethanol, propanol, ethylene glycol, propylene glycol, propane, butane, isobutane, pentane, dimethyl ether and diethyl ether in an amount from 0.1 to 50% by weight, based on the total weight of the formulation.

6. The aerosol formulation according to claim 1, further comprising a cosolvent selected from the group consisting of water, ethanol, propanol, ethylene glycol, propylene glycol, propane, butane, isobutane, pentane, dimethyl ether and diethyl ether in a amount from 0.1 to 30% by weight, based on the total weight of the formulation.

7. The aerosol formulation according to claim 1, wherein it further comprises surface-active agents in an amount from 0.001 to 0.1% by weight, based on the total weight of the formulation.

8. An inhalable medicinal aerosol formulation comprising an effective amount of a pharmaceutically active compound selected from the group consisting of beta-mimetics and corticoids, and a pressure-liquified homogenous propellant mixture comprising carbon dioxide and a hydrofluoroalkane selected from the group consisting of 1,1,1,2-tetrafluoroethane. 1,1,1,2,3,3,3-heptafluoropropane, and 1,1,1,2-tetrafluoroethane in the presence of 1,1,1,2,3,3,3-heptafluoropropane, the carbon dioxide being present in an amount of from 0.01 to 2% by weight, based on the total weight of the formulation, and the hydrofluoroalkane being present in an amount of at least 64% by weight, based on the total weight of the formulation, wherein the inhalable medicinal aerosol formulation is contained in a metered dose inhaler.

9. The aerosol formulation according to claim 8, further comprising a cosolvent selected from the group consisting of water, ethanol, propanol, ethylene glycol, propylene glycol, propane, butane, isobutane, pentane, dimethyl ether and diethyl ether in an amount from 0.1 to 30% by weight, based on the total weight of the formulation.

10. A metered dose inhaler comprising an inhalable medicinal aerosol formulation comprising an effective amount of a pharmaceutically active compound and a pressure-liquified homogeneous propellant mixture, comprising carbon dioxide and hydrofluoroalkane of formula

$C_xH_yF_z$ (I)

in which x is the number 1, 2 or 3, y and z are each an integer $\geq 1$ and y+z=2x+2,
the carbon dioxide being present in an amount of from 0.01 to 2% by weight, based on the total weight of the formulation, wherein the hydrofluoroalkane of the formula I is selected from the group consisting of 1,1,1,2-tetrafluoroethane; 1,1,1,2,3,3,3-heptafluoropropane; and 1,1,1,2-tetrafluoroethane in the presence of 1,1,1,2,3,3,3-heptafluoropropane contained in an aerosol container suitable for use as a metered dose inhaler.

11. The metered dose inhaler according to claim 10, wherein the hydrofluoroalkane of the formula I is present in an amount of at least 64% by weight, based on the total weight of the formulation.

12. The metered does inhaler according to claim 10, wherein the pharmaceutically active compound is a beta-mimetic selected from the group consisting of salbutamol, formoterol, salmoterol, fenoterol, clenbuterol, terbutaline, bambuterol, broxaterol, epinephrine, isoprenaline, orciprenaline, hexoprenaline, tulobuterol, reproterol, bamethan, and pharmaceutically acceptable salts thereof.

13. The metered does inhaler according to claim 10, wherein the pharmaceutically active compound is a corticoid selected from the group consisting of beclomethasone, betamethasone, ciclomethasone, dexamethasone, triamcinolone, budesonide, butixocort, ciclesonide, fluticasone, flunisolide, icomethasone, mometasone, tixocortol, loteprednol, and pharmaceutically acceptable salts thereof.

14. The metered dose inhaler according to claim 10, wherein said inhalable medicinal aerosol further comprises a cosolvent selected from the group consisting of water, ethanol, propanol, ethylene glycol, propylene glycol, propane, butane, isobutane, pentane, dimethyl ether and diethyl ether in an amount from 0.1 to 50% by weight, based on the total weight of the formulation.

15. The metered dose inhaler according to claim 10, wherein said inhalable medicinal aerosol further comprises a cosolvent selected from the group consisting of water, ethanol, propanol, ethylene glycol, propylene glycol, propane, butane, isobutane, pentane, dimethyl ether and diethyl ether in an amount from 0.1 to 30% by weight, based on the total weight of the formulation.

16. The metered dose inhaler according to claim 10, wherein said inhalable medicinal aerosol further comprises surface-active agents in an amount from 0.001 to 0.1% by weight, based on the total weight of the formulation.

17. A metered dose inhaler comprising an inhalable medicinal aerosol formulation comprising an effective amount of a pharmaceutically active compound selected from the group consisting of beta-mimetics and corticoids, and a pressure-liquified homogenous propellant mixture comprising carbon dioxide and a hydrofluoroalkane selected from the group consisting of 1,1,1,2-tetrafluoroethane, 1,1,1,2,3,3,3-heptafluoropropane, and 1,1,1,2-tetrafluoroethane in the presence of 1,1,1,2,3,3,3-heptafluoropropane, the carbon dioxide being present in an amount of from 0.01 to 2% by weight, based on the total weight of the formulation, and the hydrofluoroalkane being present in an amount of at least 64% by weight, based on the total weight of the formulation contained in an aerosol container suitable for use as a metered dose inhaler.

18. The metered dose inhaler according to claim 17, wherein said inhalable medicinal aerosol further comprises a cosolvent selected from the group consisting of water, ethanol, propanol, ethylene glycol, propylene glycol, propane, butane, isobutane, pentane, dimethyl ether and diethyl ether in an amount from 0.1 to 30% by weight, based on the total weight of the formulation.

* * * * *